(12) United States Patent
Van Atta et al.

(10) Patent No.: US 8,187,557 B2
(45) Date of Patent: May 29, 2012

(54) REAGENT RESERVOIR SYSTEM FOR ANALYTICAL INSTRUMENTS

(75) Inventors: Reuel Van Atta, Palo Alto, CA (US);
Dias Lourenco Francisco, Sunnyvale, CA (US)

(73) Assignee: Cepheid, Sunnyvale, CA (US)

( * ) Notice: Subject to any disclaimer, the term of this patent is extended or adjusted under 35 U.S.C. 154(b) by 909 days.

(21) Appl. No.: 11/485,944

(22) Filed: Jul. 13, 2006

(65) Prior Publication Data
US 2008/0014114 A1    Jan. 17, 2008

(51) Int. Cl.
*B01L 9/00* (2006.01)
*G01N 33/52* (2006.01)

(52) U.S. Cl. ............ 422/425; 422/401; 422/57; 422/58; 422/59; 422/100

(58) Field of Classification Search .................... 422/57, 422/58, 59, 100
See application file for complete search history.

(56) References Cited

U.S. PATENT DOCUMENTS

| | | |
|---|---|---|
| 5,587,128 A | 12/1996 | Wilding et al. |
| 5,714,380 A | 2/1998 | Neri et al. |
| 5,763,157 A | 6/1998 | Treml et al. |
| 5,776,563 A | 7/1998 | Buhl et al. |
| 5,786,182 A | 7/1998 | Catanzariti et al. |
| 5,834,254 A | 11/1998 | Shen et al. |
| 5,861,251 A | 1/1999 | Park et al. |
| 5,876,992 A | 3/1999 | De Rosier et al. |
| 6,168,948 B1 | 1/2001 | Anderson et al. |
| 6,374,684 B1 | 4/2002 | Dority |
| 6,663,833 B1 | 12/2003 | Stave et al. |
| 2003/0039589 A1* | 2/2003 | Smith .......................... 422/100 |
| 2005/0069898 A1 | 3/2005 | Moon et al. |
| 2005/0254995 A1* | 11/2005 | Sostek et al. .................... 422/56 |
| 2006/0068398 A1 | 3/2006 | McMillan et al. |

FOREIGN PATENT DOCUMENTS

WO    WO 96/00301    1/1996

OTHER PUBLICATIONS

Ready-To-Go (MT) RT-PCR Beads, instructions manual, from Amersham Biosciences, XY-073-00-06, rev. 5, copyright 1999.

* cited by examiner

*Primary Examiner* — Sally Sakelaris
(74) *Attorney, Agent, or Firm* — Kilpatrick Townsend & Stockton LLP

(57) ABSTRACT

The invention provides a reagent reservoir system and disposable reaction cassettes using the same. In one aspect, such system comprises a chamber in which dried reagent, particularly lyophilized reagent, is constrained to remain in a defined region of the chamber by a retaining member that obstructs passage of such reagents to other regions of the chamber where they may escape hydration or activation.

16 Claims, 4 Drawing Sheets

REAGENT RESERVOIR SYSTEM FOR ANALYTICAL INSTRUMENTS

FIELD OF THE INVENTION

The invention relates generally to methods and apparatus for storing and activating reagents for analytical assays, and more particularly, to methods and apparatus for storing and activating dried or lyophilized reagents.

BACKGROUND

Many important assays involve the use of labile reagents, such as peptides, enzymes, antibodies, or other compounds that are readily degraded outside narrow environmental ranges. Such assays include enzyme-based nucleic acid amplification assays, immunoassays, enzyme substrate assays, and the like. The sensitivity of these reagents not only makes routine handling and transport more difficult, but also often limits the application of such assays outside of research settings, since opportunities are not available to provide fresh reagents or to monitor the properties or activities of the reagents. These are significant limitations in view of the great interest in using these assays for a host of important monitoring tasks, frequently in outdoor settings, where transport, environmental control, and ready access to instrumentation used with the assays may be limited or unavailable. Examples of such monitoring applications include bio-defense monitoring, agricultural and livestock monitoring, pathogen testing, acute care medical applications, and the like.

Some problems related to the lability of protein assay reagents have been addressed by lyophilization, or freeze-drying, e.g. Franks et al, U.S. Pat. No. 5,098,893; Cole, U.S. Pat. No. 5,102,788; Shen et al, U.S. Pat. No. 5,556,771; Treml et al, U.S. Pat. No. 5,763,157; De Rosier et al, U.S. Pat. No. 6,294,365; Buhl et al, U.S. Pat. No. 5,413,732; and the like. However, when freeze-dried reagents are used as powders or other small particulates, difficulties can arise in controlling their disposition in containers or reaction chambers because of static charges carried by the particulates, e.g. Matsusaka et al (2002), Advanced Powder Technol., 13: 157-166. This is particularly troublesome in disposable plastic or solid polymer cartridges that are pre-loaded with such particulates or powders and can easily lead to cartridge-to-cartridge measurement variability because the lyophilized particulates become inappropriately dispersed and are not re-hydrated completely.

It would be useful if reagent storage components or cartridges were available that could be pre-loaded with lyophilized particulates, or like materials, and that would permit complete re-hydration of reagents in desired concentrations and amounts with minimum possibility of being dispersed to areas out of contact with a re-hydrating or activating solution.

SUMMARY OF THE INVENTION

In one aspect, the invention provides a reagent reservoir system in which dried reagents are constrained to remain in a defined region of a chamber by a simple inert member that obstructs passage of such reagents to regions where they may escape hydration or activation. In one aspect, the invention includes a reagent reservoir system comprising: (i) a chamber for holding a reagent, the chamber having a longitudinal axis, a fluid port, a reagent holding end, and an exhaust port that permits gas in the chamber to exit when a liquid is transferred to the chamber through the fluid port, the exhaust port being disposed in the chamber at an end opposite to that of the reagent holding end with respect to the longitudinal axis; (ii) a dried reagent disposed in the reagent holding end of the chamber, the dried reagent being capable of dissolving in liquid transferred to the chamber; and (iii) a retaining member movably disposed in the chamber between the exhaust port and the dried reagent, the retaining member obstructing passage of the dried reagent so that when activation liquid is transferred to the chamber and collects in the reagent holding end of the chamber the dried reagent dissolves in the liquid to activate the reagent without passing the retaining member.

In another aspect, the invention includes a disposable reaction cassette for conducting an assay on a sample, such disposable reaction cassette comprising: (i) a lysis reservoir having a fluid port, the lysis reservoir being capable of holding a lysis buffer; (ii) a sample chamber having a sealable port at a first end and a fluid port at a second end, the sample chamber being capable of forming a fluidly closed chamber whenever the sealable port is closed and the sample chamber being selectably in fluid communication with the lysis reservoir; (iii) a reagent chamber having an exhaust port at a first end, a fluid port and a dried reagent at a second end, and movably disposed therebetween, a retaining member that obstructs passage of the dried reagent through the chamber, wherein the reagent chamber is selectably in fluid communication with the sample chamber; and (iv) a reaction chamber having an inlet and an outlet, the reaction chamber being selectably in fluid communication with the reagent chamber.

In still another aspect, the invention provides a reagent reservoir for storing and activating a dried reagent, the reagent reservoir comprising: (i) a chamber having a first end and a second end along a longitudinal axis, the second end being capable of holding dried reagent; (ii) an exhaust port at the first end; (iii) a fluid port at the second end; and (iv) a retaining member movably disposed between the first and second ends, such that when dried reagent is held in the second end, the retaining member obstructs passage of the dried reagent to the first end. In a preferred embodiment, the retaining member is buoyant in liquid (e.g., has a density less than the density of water which is 1,000 kg/m³) such that when an activation liquid is transferred to the second end by the fluid port, the buoyant retaining member is buoyed to a top surface of the liquid.

In another aspect, dried reagents for use with the invention include lyophilized particulates, especially those containing reagents for enzyme-based assays, such as nucleic acid amplification assays.

DEFINITIONS

Figure 1A:
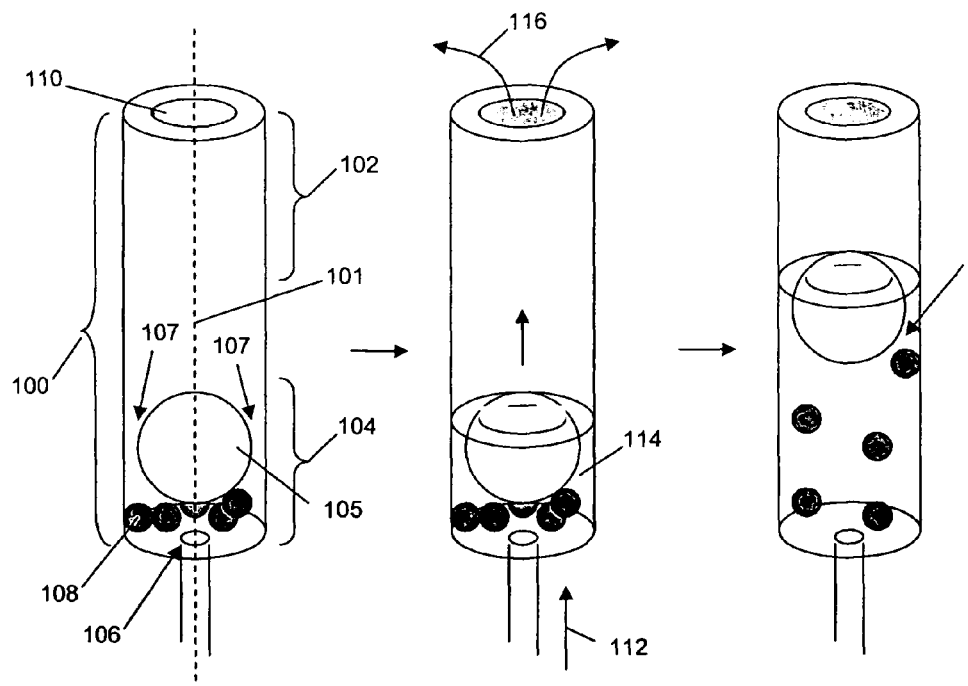
FIGS. 1A-1C illustrate several embodiments and the operation of a reagent reservoir system of the invention.
Figure 1A:
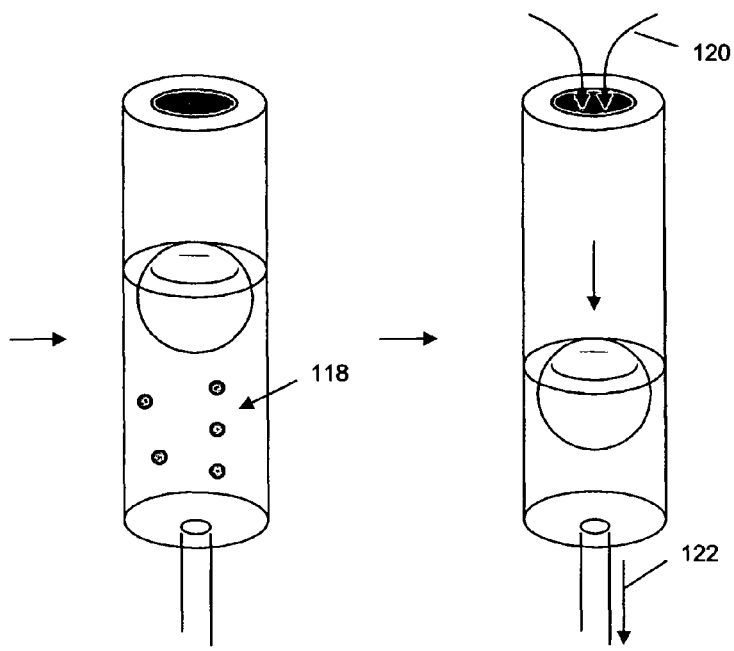

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Sambrook et al, Molecular Cloning: A Laboratory Manual, $2^{nd}$ Edition (Cold Spring Harbor Laboratory, 1989); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, to a target sequence or its complement is required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, ligase chain reactions (LCRs), strand-displacement reactions (SDAs), nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Landegren et al, U.S. Pat. No. 4,988,617 ("LCR"); Birkenmeyer et al, U.S. Pat. No. 5,427,930 ("gap-LCR"); Kacian et al, U.S. Pat. No. 5,399,491 ("NASBA"); Walker, U.S. Pat. Nos. 5,648,211; 5,712,124 ("SDA"); Lizardi, U.S. Pat. No. 5,854,033; Aono et al, Japanese patent publ. JP 4-262799 (rolling circle amplification); and the like. In one aspect, amplicons are produced in a temperature-cycling amplification reaction that includes repeated steps of denaturing reaction products, usually double stranded DNA, at a first temperature, and annealing primers for polymerase extension at a second temperature. A temperature-cycling amplification reactions of special interest are PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Closed" in reference to an amplification reaction means that such reaction takes place within a vessel or container or chamber that has no openings through which liquids may pass, in particular, liquids that contain non-sample materials, such as, non-sample biomolecules or organisms, including, but not limited to, nucleic acids, proteins, viruses, bacteria, or the like. In one aspect, a vessel, chamber, or container containing a closed amplification reaction may include a port or vent that is gas permeable but liquid impermeable, for example, a port that permits the venting of air through a filter membrane but not liquids under conventional reaction conditions. Suitable membranes for such ports or vents include woven polyolefin films, such as Tyrek® film (DuPont), or the like.

"Fluidly closed" means that, under conventional operating conditions, liquids within a system that comprises one or more vessels, chambers, valves, and/or passages, possibly interconnected and in communication with one another, cannot communicate with the exterior of such a system, and likewise liquids on the exterior of such a system cannot communicate with liquids contained within the interior of the system. In one aspect, conventional operating conditions means that vessels, chambers, valves, and passages of a fluidly closed system are pressurized to an extent less than 100 psi, or in another aspect, to an extent less than 50 psi, or to an extent less than 30 psi.

"Indicator" means a probe that is capable of generating an optical signal in the presence of a product of an amplification reaction (i.e. an "amplification product") such that as product accumulates in the reaction mixture the optical signal of the indicator increases, at least over a predetermined range of concentrations. The optical signals includes, but are not limited to, fluorescent signals, chemiluminescent signals, electrochemiluminescent signals, calorimetric signals, and the like. "Fluorescent indicator" means an indicator capable of generating a fluorescent signal in the presence of a product of an amplification reaction (i.e. an "amplification product") such that as product accumulates in the reaction mixture the signal of the fluorescent indicator increases, at least over a predetermined range of concentrations. Fluorescent indicators may be non-specific, such as intercalating dyes that bind to double stranded DNA products, e.g. YO-PRO-1, SYBR green 1, and the like, Ishiguro et al, Anal. Biochem., 229: 207-213 (1995); Tseng et al, Anal. Biochem., 245: 207-212 (1997); Morrison et al, Biotechniques, 24: 954-962 (1998); or such as primers having hairpin structures with a fluorescent molecule held in proximity to a fluorescent quencher until forced apart by primer extension, e.g. Whitecombe et al, Nature Biotechnology, 17: 804-807 (1999) ("Amplifluor™ primers"). Fluorescent indicators also may be target sequence specific, usually comprising a fluorescent molecule in proximity to a fluorescent quencher until an oligonucleotide moiety to which they are attached specifically binds to an amplification product, e.g. Gelfand et al, U.S. Pat. No. 5,210,015 ("taqman"); Nazarenko et al, Nucleic Acids Research, 25: 2516-2521 (1997) ("scorpion probes"); Tyagi et al, Nature Biotechnology, 16: 49-53 (1998) ("molecular beacons"). Fluorescent indicators may be used in connection with real-time PCR, or they may be used to measure the total amount of reaction product at the completion of a reaction.

"Internal standard" means a nucleic acid sequence that is amplified in the same amplification reaction as a target polynucleotide in order to permit absolute or relative quantification of the target polynucleotide in a sample. An internal standard may be endogenous or exogenous. That is, an internal standard may occur naturally in the sample, or it may be added to the sample prior to amplification. In one aspect, multiple exogenous internal standard sequences may be added to a reaction mixture in a series of predetermined concentrations to provide a calibration to which a target amplicon may be compared to determine the quantity of its corresponding target polynucleotide in a sample. Selection of the number, sequences, lengths, and other characteristics of exogenous internal standards is a routine design choice for one of ordinary skill in the art. Preferably, endogenous internal standards, also referred to herein as "reference sequences," are sequences natural to a sample that correspond to minimally regulated genes that exhibit a constant and cell cycle-independent level of transcription, e.g. Selvey et al, Mol. Cell Probes, 15: 307-311 (2001). Exemplary reference sequences include, but are not limited to, sequences from the following genes: GAPDH, $\beta_2$-microglobulin, 18S ribosomal RNA, and β-actin (although see Selvey et al, cited above).

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes. In the context of the present invention, kits include a disposable reaction cassette comprising a reagent reservoir system of the invention.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, and a detection system. Microfluidics may further include valves, pumps, and specialized functional coatings on their interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 µm to about 0.1 µm. Microfluidics devices typically have volume capacities in the range of from 1 µL to a few nL, e.g. 10-100 nL. The fabrication and operation of microfluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437.

"Nucleic acid sequence-based amplification" or "NASBA" is an amplification reaction based on the simultaneous activity of a reverse transcriptase (usually avian myeloblastosis virus (AMV) reverse transcriptase), an RNase H, and an RNA polymerase (usually T7 RNA polymerase) that uses two oligonucleotide primers, and which under conventional conditions can amplify a target sequence by a factor in the range of $10^9$ to $10^{12}$ in 90 to 120 minutes. In a NASBA reaction, nucleic acids are a template for the amplification reaction only if they are single stranded and contain a primer binding site. Because NASBA is isothermal (usually carried out at 41° C. with the above enzymes), specific amplification of single stranded RNA may be accomplished if denaturation of double stranded DNA is prevented in the sample preparation procedure. That is, it is possible to detect a single stranded RNA target in a double stranded DNA background without getting false positive results caused by complex genomic DNA, in contrast with other techniques, such as RT-PCR. By using fluorescent indicators compatible with the reaction, such as molecular beacons, NASBAs may be carried out with real-time detection of the amplicon. Molecular beacons are stem-and-loop-structured oligonucleotides with a fluorescent label at one end and a quencher at the other end, e.g. 5'-fluorescein and 3'-(4-(dimethylamino)phenyl)azo) benzoic acid (i.e., 3'-DABCYL), as disclosed by Tyagi and Kramer (cited above). An exemplary molecular beacon may have complementary stem strands of six nucleotides, e.g. 4 G's or C's and 2 A's or T's, and a target-specific loop of about 20 nucleotides, so that the molecular beacon can form a stable hybrid with a target sequence at reaction temperature, e.g. 41° C. A typical NASBA reaction mix is 80 mM Tris-HCl [pH 8.5], 24 mM $MgCl_2$, 140 mM KCl, 1.0 mM DTT, 2.0 mM of each dNTP, 4.0 mM each of ATP, UTP and CTP, 3.0 mM GTP, and 1.0 mM ITP in 30% DMSO. Primer concentration is 0.1 µM and molecular beacon concentration is 40 nM. Enzyme mix is 375 sorbitol, 2.1 µg BSA, 0.08 U RNase H, 32 U T7 RNA polymerase, and 6.4 U AMV reverse transcriptase. A reaction may comprise 5 µL sample, 10 µL NASBA reaction mix, and 5 µL enzyme mix, for a total reaction volume of 20 µL. Further guidance for carrying out real-time NASBA reactions is disclosed in the following references that are incorporated by reference: Polstra et al, BMC Infectious Diseases, 2: 18 (2002); Leone et al, Nucleic Acids Research, 26: 2150-2155 (1998); Gulliksen et al, Anal. Chem., 76: 9-14 (2004); Weusten et al, Nucleic Acids Research, 30(6) e26 (2002); Deiman et al, Mol. Biotechnol., 20: 163-179 (2002). Nested NASBA reactions are carried out similarly to nested PCRs; namely, the amplicon of a first NASBA reaction becomes the sample for a second NASBA reaction using a new set of primers, at least one of which binds to an interior location of the first amplicon.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified. Typically, the number of target sequences in a multiplex PCR is in the range of from 2 to 10, or from 2 to 6, or more typically, from 2 to 4.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, β$_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" and "oligonucleotide" are used interchangeably and each means a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2$^{nd}$ Edition (Cold Spring Harbor Press, New York, 2003).

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like. Likewise, a readout of a real-time PCR can be one or more fluorescent intensity signals within specified frequency bands as functions of time, or other reaction parameter related to time.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecule in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

"Tm" or "melting temperature" means the temperature at which a population of double-stranded nucleic acid molecules becomes half dissociated into single strands. Several equations for calculating the Tm of nucleic acids are well known in the art. For example, a simple estimate of the Tm value may be calculated by the equation. $Tm=81.5+0.41$ (% G+C), when a nucleic acid is in aqueous solution at 1 M NaCl. Methods for calculating Tm based on more complete models of duplex formation and dissociation are found in Breslauer et al, Proc. Natl. Acad. Sci., 83: 3746-3750 (1986); and Wetmur, Crit. Rev. Biochem. Mol. Biol., 26: 227-259 (1991).

"Sample" means a quantity of material from a biological, environmental, medical, or patient source in which detection or measurement of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. The terms "sample" and "specimen" are used interchangeably.

DETAILED DESCRIPTION OF THE INVENTION

The practice of the present invention may employ, unless otherwise indicated, conventional techniques and descriptions of organic chemistry, polymer technology, molecular biology (including recombinant techniques), cell biology, biochemistry, and analytical instrumentation, which are within the skill of the art. Such conventional techniques include fluorescence measurement, optical signal collection, instrumentation control, data analysis, electronics, mechanical engineering, fluid handling, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), as well as other treatises and guides cited below.

The invention is directed to reagent reservoir systems and disposable reaction cassettes employing such systems. The invention addresses problems associated with the storage and activation of assay reagents, particularly proteins, which have been at least partially dehydrated and embedded in a protective matrix so that solid or semi-solid precipitates or particles are formed. Such solid and semi-solid masses in particulate or powder form often have physical properties, such as electrostatic charge, that make them difficult to control, since the charge-carrying particulates may be attracted to regions of a vessel or reservoir where there is no contact with an activating liquid (e.g., a solution or buffer). In one aspect, such problems are overcome by providing a reagent reservoir system comprising a chamber having an elongated shape and containing a retaining member (preferably buoyant) that obstructs passage of reagent-containing solids or semi-solids, referred to herein as "lyophilized particulates," thereby restricting their dispersal through the chamber. That is, the retaining member prevents the dried reagent, but neither gases nor liquids, from entering the region between a first end of the chamber and the retaining member. The chamber further comprises an exhaust port at the first end and a fluid port at the end of the chamber containing the dried reagent (i.e., a second end). The first end with the exhaust port, the retaining member and the second end with the fluid port and containing dried reagent are disposed along the longitudinal axis of the chamber.

In a preferred embodiment, the retaining member floats, or is buoyant, in whatever activation liquid is employed to hydrate and/or activate the dried reagent. In one aspect, such buoyancy is obtained by making the buoyant retaining member from a material having a lower specific gravity than that of the activation liquid; however, it may also be a heterogeneous structure having an average specific gravity less than that of the activation liquid. Preferably, the buoyancy of the retaining member in the activation liquid is selected so that 75 to 90 percent of the volume of the buoyant retaining member is submerged. Optionally, a chamber also contains a fixed retaining member that is disposed in the region of the chamber to the side of the buoyant retaining member opposite that occupied by the dried reagent. The function of the fixed retaining member includes obstructing passage of the buoyant retaining member (but not the passage of liquids or gases). The fixed retaining member may be fabricated as an integral piece of the chamber of it can be a separate piece that is placed in the chamber during assembly. In either case, placement of the fixed retaining member allows one to control the extent of travel of the buoyant retaining member inside of the chamber. When a fixed retaining member is employed, the buoyant retaining member further prevents dried reagent (e.g., lyophilized particulates) from (i) coming into contact with (and sticking to or precipitating on) crevices or edges of the fixed retaining member by foaming action in the activation liquid, and (ii) becoming trapped in the surface tension of the activation liquid so that incomplete solvation occurs. Preferably, the fixed retaining member is disposed in the chamber at a position that permits the formation of a gap between it and the buoyant retaining member and lyophilized particulates whenever the longitudinal axis of the chamber is in a vertical orientation (in the absence of liquid).

As discussed more fully below, the invention further provides disposable reaction cassettes that incorporate one or more reagent reservoir systems.

Figure 1B:
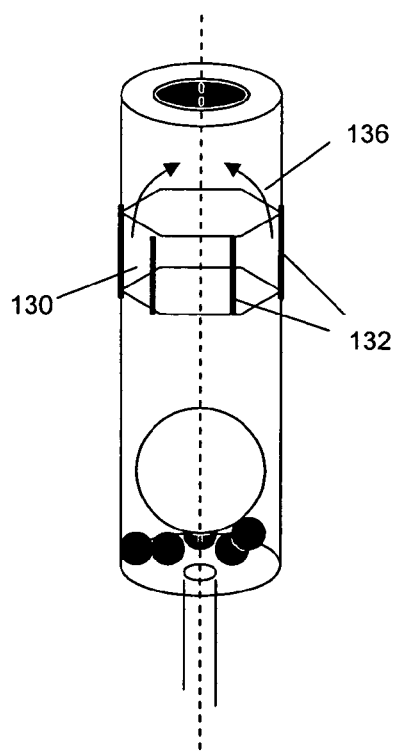
Figure 1C:
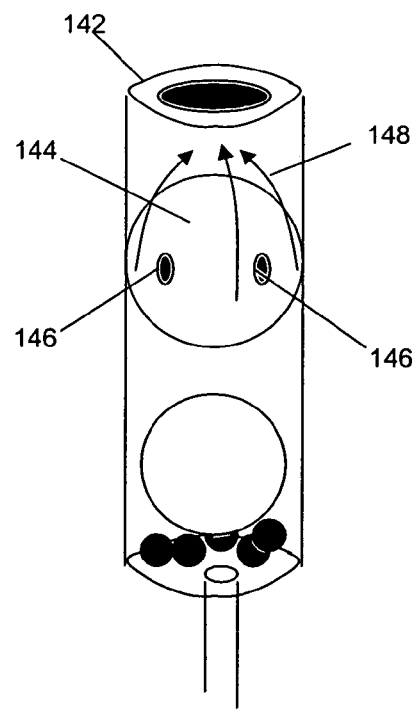

The above principles of the invention are illustrated by the embodiments shown in FIGS. 1A-1C. FIG. 1A illustrates the operation of an embodiment that does not include a fixed retaining member and FIGS. 1B and 1C illustrate two embodiments that include two different kinds of fixed retaining members. In FIG. 1A, elongated chamber (100) having longitudinal axis (101) is shown in a vertical orientation with first end (102) at the top and second end (104) at the bottom, which is the preferred orientation whenever gravity or positive or negative pressure is used to force liquid in or out of chamber (100). Buoyant retaining member (105) rests at second end (104) on top of dried reagent, shown as lyophilized particulates (108), preventing their dispersal to first end (102). The inside diameter of chamber (100), diameter and/or shape of buoyant retaining member (105), and the diameter and/or shape of lyophilized particulates (108) are selected so that gaps (107) between the inner wall of chamber (100) and outer surface of buoyant retaining member (105) do not allow passage of lyophilized particulates (108), particularly prior to transfer of liquid to chamber (100). In one aspect, the chamber, buoyant retaining member, and fixed retaining member are made of a suitable plastic or polymeric solid, such as polystyrene, polyvinylchloride, polycarbonate, polypropylene, polyethylene, or any other plastic that is rigid and inert with respect to the fluids and reagents used with the system.

Exhaust port (110) is located at first end (102) and fluid port (106) is located at second end (104). Activation liquid (114) is transferred through passage (112) and fluid port (106) to the interior of chamber (100) thereby floating buoyant retaining member (105). Activation liquid (114) is typically an aqueous solution or suspension or a buffer such as water. In some embodiments, the liquid contains the analyte (e.g., nucleic acid) to be tested with the reagent(s) stored in the chamber. Gas displaced by activation liquid (114) escapes (116) through exhaust port (110). Preferably, exhaust port (110) comprises a gas permeable and liquid impermeable membrane, such as a woven polyolefin film, for example, Tyrek® film (DuPont), or the like. Lyophilized particulates (108) dissolve (118) in activation liquid (114) to form a functional reagent for an assay, while a predetermined amount of activation liquid (114) is loaded into chamber (100), and optionally during a predetermined incubation period thereafter. The latter predetermined incubation time depends on the nature and solubility properties of the reagents and other compounds making up lyophilized particulates (108). Chamber (100) could also be subjected to heating and mixing steps to assist the dissolution of lyophilized particulates (108). Once a functional reagent solution is formed, it is removed (122) from chamber (100) through fluid port (106) for use in an assay. Movement of liquids in and out of chamber (100) can be accomplished in many different ways well known to those of ordinary skill in the art, such increasing or decreasing pressure on the liquid by a pump, driving liquid out of the chamber by increasing gas pressure by way of exhaust port (110), using gravity to drain the liquid, and the like. In other embodiments, more than one fluid port can be used. For example, separate inlet and outlet ports may be used, and in such cases, one of the ports may be located at first end (102), or at other locations in chamber (100).

Although the preferred embodiment includes a buoyant retaining member, alternative embodiments may employ a non-buoyant retaining member (having a density greater than the activation liquid). In these alternative embodiments, when the liquid is added to the chamber, the retaining member sinks to the bottom of the chamber when the dried reagent dissolves in the liquid. In these alternative embodiments, the fluid port may be offset from the bottom of the chamber to prevent any problems in removing the reagent solution from the chamber (e.g., so that the non-buoyant retaining member does not block the port).

In a preferred embodiment, the reagent reservoir system further comprises a fixed retainer member disposed along longitudinal axis (101) between first end (102) and buoyant retaining member (105). As mentioned above, a fixed retaining member can be implemented in many ways for carrying out its primary function of obstructing passage of buoyant retaining member (105) without obstructing passage of either gases or liquids. The implementation selected depends on conventional factors of instrument design, including cost of materials, ease of manufacture, ease of assembly, and the like. FIGS. 1B and 1C illustrate two exemplary embodiments of fixed retainer members. In FIG. 1B, fixed retaining member (130) has a hexagonal cross section and is closely fitted into the interior of chamber (100) so that it is immobilized by contact of edges (132) with the inner wall of chamber (100). Between edges (132) there are gaps that allow passage (136) of gas or liquid. Alternatively, a chamber (100) can be provided that has a transverse cross section (142) that is not circular, so that a spherically shaped fixed retaining member (144) can be fitted, or wedged, into the interior of chamber (100) and immobilized by contacts (146) with the inner wall of chamber (100). Since cross section of chamber (100) is not circular, gaps are present for gas or liquid to pass (148).

In one aspect, the invention provides disposable reaction cassettes that employ one or more reagent reservoir systems described above. Such reaction cassettes can be designed to perform many different kinds of assays and are typically used with an apparatus that provides ancillary functions, such as temperature control, detection systems, mechanical or electrical power sources to pump, or otherwise move, liquids into and out of cassettes, and the like. Such reaction cassettes can vary widely is shape and scale, from macro-scale, e.g. reaction volumes, reservoir volumes, sample volumes, in 1-10 mL range, to micro-scale, e.g. reaction volumes, reservoir volumes, sample volumes in nanoliter to microliter range. Exemplary systems that may be used with reagent reservoir systems of the invention include fluidly closed reaction systems employing a rotary valve and a piston-type fluid pump under microprocessor control, such as disclosed in Christel et al, U.S. Pat. No. 6,369,893 and Dority, U.S. Pat. No. 6,374,684; and microfluidics devices, such as disclosed in the references cited under Definitions, and further disclosed in Shoji et al, Appl. Biochem. Biotechnol., 41: 21-34 (1993) and J. Micromech. Microeng., 4: 157-171 (1994); McCormick et al, Anal. Chem., 69: 2626-2630 (1997); Cheng et al, Topics Curr. Chem., 194: 215-231 (1998); Stave et al, U.S. Pat. No. 6,663, 833; Neri et al, U.S. Pat. No. 5,714,380; Northrup et al, U.S. Pat. No. 5,589,136; and the like. Additional reaction cassette system that can be used with the present invention include Petersen et al, U.S. patent publication 2005/0042137; and Taylor et al, U.S. patent publication 2004/0166031; Catanzariti et al, U.S. Pat. No. 5,786,182; and Itoh et al, U.S. patent publication 2005/0180880; which are incorporated by reference. Such systems are capable of fluidly transferring reactants, samples, and reaction products between reservoirs and reaction chambers in a controlled manner. That is, such systems move reactants, samples, reaction products, and the like, in liquid solutions under liquid-moving force in a directed manner. Liquid-moving forces include differential pressure generated by various kinds of pumps or compressed gas reservoirs, electrokinetic pumps, and the like.

In one aspect, disposable reaction cassettes of the invention may be conveniently implemented by specific designs and methods of operation of rotary valves, reactant and waste reservoirs, and reaction chambers generally disclosed in Dority (cited above). In another aspect, in which real-time monitoring of amplification reactions is desired, such apparatus is conveniently used with the temperature controller and fluorometer disclosed by Christel et al (cited above).

Figure 2A:
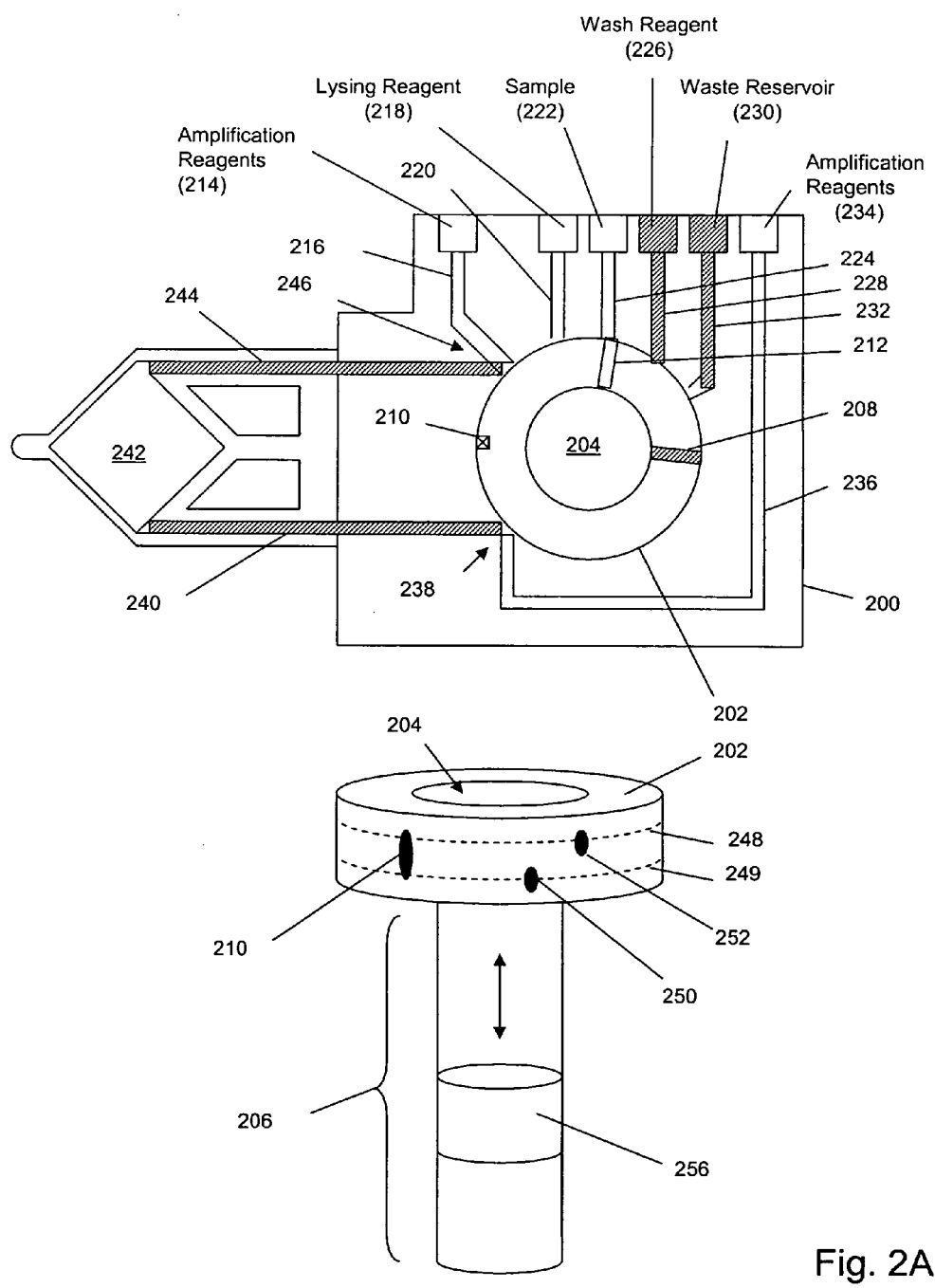
FIGS. 2A-2B diagrammatically illustrate an embodiment of a disposable reaction cassette that employs a reagent reservoir system of the invention.
Figure 2B:
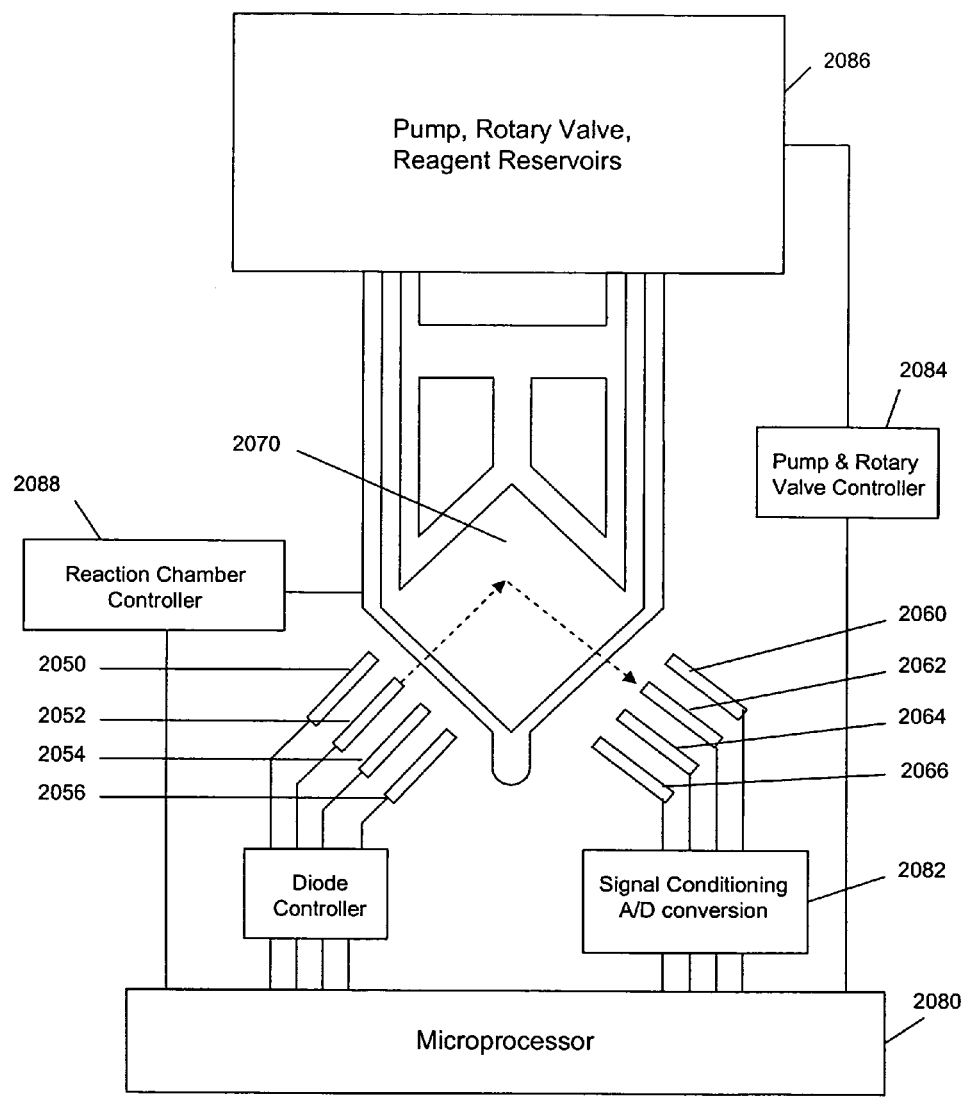

FIG. 2A shows diagrammatically a disposable reaction cassette that follows the general design approach disclosed in Dority (cited above) for carrying out amplification reactions to amplify target polynucleotides from a sample under fluidly closed conditions. As mentioned above, such a disposable reaction cassette may be used with a detection apparatus disclosed by Christel et al (cited above) and illustrated diagrammatically in FIG. 2B. After a sample or specimen is loaded into the reaction cassette and pre-conditioned, e.g. by disrupting tissue, lysing cells, and the like, the resulting solution is fluidly transferred to a sample reservoir from which one or more portions are dispensed to a reagent reservoir system under programmed control for mixing with amplification reagents to form a reaction mixture. The reaction mixture is then fluidly transferred to a reaction chamber where an amplification reaction takes place.

FIG. 2A shows housing (200) that contains rotary valve (202) having internal chamber (204) that is operationally connected to piston-type pump (206). Up-strokes of piston (256) of pump (206) pressurize chamber (204) and force fluid contents out through whatever ports that may be in communication with reservoirs or the like; likewise, down strokes of piston (256) of pump (206) depressurize chamber (204) and draw fluids in through whatever ports may be open and in communication with reservoirs or the like. Further descriptions of the operation and construction of such pump-rotary valve devices and the use of chamber (204) for sample preparation is provided by Dority (cited above), which is incorporated by reference for this purpose. Rotary valve (202) has various ports, for example (250) and (252), and associated passages, (208) and (212), that permit chamber (204) to be in fluid communication with various reservoirs (described more fully below) or reaction chamber (242) whenever such ports are aligned with corresponding ports to passages to such reservoirs or reaction chamber (242). In the present exemplary embodiments, the longitudinal axes of such associated passages are radially disposed in rotary valve (202) within either one of two planes perpendicular to the axis of rotary valve (202)(shown with dashed lines (248) and (249)), such that chamber (204) may be placed in fluid communication with ports of passages to reservoirs, and the like, disposed in housing (200). Rotary valve (202) further includes connecting passages (210), (211), and (213), which permit a port in one plane of the valve to be placed in fluid communication with ports of housing (200) that are in the other plane of rotary valve (202). Such connection passages do not permit fluid communication with interior chamber (204). As illustrated in FIG. 2A, when such connecting passages are aligned at (246) with ports of passages (244) and (216), passages (244) and (216) are in fluid communication. Likewise, when such connecting passages are aligned at (238) with ports of passages (240) and (236), passages (240) and (236) are in fluid communication. In FIG. 2A, cross-hatched passages and reservoirs in housing (200) are in the pump-proximal plane of rotary valve (202) (illustrated in the bottom panel of FIG. 2A by dotted line (249)), whereas the non-hatched passages and reservoirs are in the pump-distal plane (illustrated in the bottom panel of FIG. 2A by dotted line (248)). As mentioned above, rotary valve (202) may place interior chamber (204) in fluid communication with various reservoirs and reaction chamber (242) that are connected by passages and have ports in the seat of housing (200) that rotary valve (202) rotates within. In the present example, such reservoirs include the following; (i) reagent reservoir system (214) containing first amplification reagents, which may be fluidly connected to rotary valve (202) by passage (216); (ii) reservoir (218) containing lysing reagents, for example, for disrupting surface membranes of cellular samples, which reservoir may be fluidly connected to rotary valve (202) by passage (220); (iii) sample reservoir (222) containing sample or specimen material, which may be fluidly connected to rotary valve (202) by passage (224); (iv) reservoir (226) containing wash solution, or wash reagent, which may be fluidly connected to rotary valve (202) by passage (228); (v) waste reservoir (230), which may be fluidly connected to rotary valve (202) by passage (232); and (vi) reagent reservoir system (234) containing second amplification reagents, which may be fluidly connected to rotary valve (202) by passage (236). It should be clear from the above example that design of rotary valve (202), e.g. selection of the number and kind of passages, and the selection of the number and type of reagent reservoirs in housing (200) is a matter of routine design choice of one of ordinary skill in the art.

A variety of instrumentation systems may be employed to implement assay reactions in disposable reaction cassettes so that an optical signal is generated related to one or more reaction parameters, such as amplicon concentration. As described more fully below, in one aspect, a multichannel optical detection system disclosed by Christel et al, U.S. Pat. No. 6,369,893 is well-suited for such measurements. A schematic of such a system applicable to the present invention is illustrated in FIG. 2C. Christel et al provide diode lasers (2050) through (2056) for illuminating a reaction mixture in reaction chamber (2070). Fluorescence excited by laser diodes (2050) through (2056) is collected by detectors (2060) through (2066), which typically are each operationally associated with a bandpass filter that restricts the wavelength of light that is detected. The excitation beams of laser diodes (2050) through (2056) may be the same or different. In one aspect, bandpass filters are selected to selectively pass fluorescence emitted by a plurality of spectrally resolvable fluorescent dyes so that each detector (2060) through (2066) collects fluorescence primarily from only one of the plurality of fluorescent dyes. For use with the present invention, one of the laser diode-detector pairs, for example (2052) and (2062), is allocated to detecting the fluorescent signal from an amplicon corresponding to a target polynucleotide, and one of the laser diode-detector pairs, for example (2056) and (2066), is allocated to detecting fluorescent signal from an amplicon corresponding to a reference sequence.

Control of all components of the detection system and fluidly closed reaction system (2086) are controlled by microprocessor (2080). Optical signals collected by detectors (2060) through (2066) are processed by conventional optics and converted into electrical signals, which, after conventional pre-amplification and conditioning (2082), are digitized for storage and/or further processing by microprocessor (2080). In one aspect of the invention, microprocessor (2080) is programmed to continuously monitor the value of the signal collected by one of the detectors, such as detector (2062). When the value reaches or exceeds a predetermined level, then microprocessor (2080) initiates a subroutine that provides controllers (2084) with a series of commands to actuate components of fluidly closed reaction system (2086) to initiate a subsequent step in the assay being conducted. Microprocessor (2080) also changes and/or regulates the temperature of reaction chamber (2070) through controller (2088). In embodiments employing closed-loop control, microprocessor (2080) may calculate values of characteristics of intensity versus time curves at predetermined intervals so that they may be compared to a predetermined level. When such calculated value reaches or exceeds a predetermined level, then microprocessor (2080) initiates the subroutine to start a subsequent assay step.

STORED REAGENTS AND ASSAYS

The nature, composition, and method of producing dried compounds for storing assay reagents (referred to herein as "dried reagent") vary widely and the formulation and production of such materials is well-known to those of ordinary skill in the art as evidenced by the following references that are incorporated by reference: Franks et al, U.S. Pat. No. 5,098,893; Cole, U.S. Pat. No. 5,102,788; Shen et al, U.S. Pat. No. 5,556,771; Treml et al, U.S. Pat. No. 5,763,157; De Rosier et al, U.S. Pat. No. 6,294,365; Buhl et al, U.S. Pat. No. 5,413,732; McMillan, U.S. patent publication 2006/0068398; McMillan et al, U.S. patent publication 2006/0068399; Schwegman et al (2005), Pharm. Dev. Technol., 10: 151-173; Nail et al (2002), Pharm. Biotechnol., 14: 281-360; and the like. Dried reagents include, but are not limited to, solid and/or semi-solid particulates, powders, tablets, crystals, capsules, beads, spheres and the like, that are manufactured in a variety of ways. In one aspect, dried reagent comprises one or more lyophilized particulates such as reagent beads or spheres.

Lyophilized particulates may have uniform compositions, wherein each particulate has the same composition, or they may have different compositions, such that two or more different kinds of lyophilized particulates having different compositions are mixed together. Lyophilized particulates can contain reagents for all or part of a wide variety of assays and biochemical reactions, including immunoassays, enzyme-based assays, enzyme substrate assays, DNA sequencing reactions, and the like. Of particular interest are assays that involve the amplification of nucleic acids, i.e. the production of amplicons, including PCRs, NASBAs, rolling circle reactions, ligase-based reactions, and the like. In one aspect, a lyophilized particulate of the invention comprises an excipient and at least one reagent of an assay.

Lyophilized particulates may be manufactured in predetermined sizes and shapes, which may be determined by the type of assay being conducted, desired reaction volume, desired speed of dissolution, and the like. In one embodiment, for example in devices designed in accordance with Dority (cited above), lyophilized particulates have a spherical shape having a diameter in the range of form 0.5 to 5 mm; that is, the lyophilized particulates are in the form of beads. Excipients are usually inert substances added to a material in order to confer a suitable consistency or form to the material. A large number of excipients are known to those of skill in the art and can comprise a number of different chemical structures. Examples of excipients, which may be used in the present invention, include carbohydrates, such as sucrose, glucose, trehalose, melezitose, dextran, and mannitol; proteins such as BSA, gelatin, and collagen; and polymers such as PEG and polyvinyl pyrrolidone (PVP). The total amount of excipient in the lyophilized bead may comprise either single or multiple compounds. In some embodiments, the type of excipient is a factor in controlling the amount of bead hygroscopy. Lowering bead hygroscopy can enhance the bead's integrity (accuracy of weighing beads) and cryoprotectant abilities. However, removing all water from the bead would have deleterious effects on those reaction components, proteins for example, that require certain amounts of bound water in order to maintain proper conformations. In general, the excipient level in the beads should be adjusted to allow moisture levels of less than 3%. In some embodiments, the excipient is trehalose, mannitol, dextran, or combinations thereof. The amount of excipient is also a factor in controlling the amount of bead hygroscopy. There are limits to the amount of excipient which can be added to form a bead. If the amount of excipient is too low, the material does not coalesce to form a bead-like shape. At the high end, excipient amounts are limited by the solubility of the excipient in the bead buffer formulation. The amount is also dependent upon the properties of the excipient. In an exemplary embodiment, trehalose is present from between 5% to 20% (w/v). In another exemplary embodiment, mannitol is present from between 2% to 20% (w/v). In yet another exemplary embodiment, mannitol is present from between 2% to 20% (w/v) and dextran is present from between 0.5% to 5% (w/v). In still another exemplary embodiment, mannitol is present in the lyophilized bead in a weight percentage of between 40% to 75% (w/w). The symbol "w/w" refers to the dry weight of the excipient divided by the dry weight of the lyophilized bead. The symbol "w/v" refers to the dry weight (in grams) of the excipient divided by the volume (in 100 mL) of the bead buffer formulation.

As mentioned above, beads or lyophilized particulates containing reagents for nucleic acid amplification reactions are of special interest, particularly reagents for PCR. In some embodiments, lyophilized particulates for PCR may comprise a mixture of compositions such that one set of lyophilized particulates, or beads, comprises a buffer, excipient, a carrier protein, magnesium, and an antifoam agent, and another set of beads may comprise generic assay components, such as a DNA polymerase (Taq polymerase, polymerases complexed with hot start antibodies such as Platinum polymerases (Invitrogen, Carlsbad, Calif.)), RNA polymerase, reverse transcriptase, and/or deoxynucleoside triphosphates (e.g., dATP, dCTP, dTTP, dGTP), and yet another set of beads may comprise specific assay components, such as primers which correspond a particular DNA sequence of interest, as well as probes which will detect the presence of primer hybridization with the DNA sequence of interest.

By way of example, lyophilized particulates for carrying out a PCR comprise the following reagents: (1) Oligonucleotide Primers. The oligonucleotides that are used in a PCR as well as oligonucleotides designed to detect amplification products can be chemically synthesized. These oligonucleotides can be labeled with radioisotopes, chemiluminescent moieties, or fluorescent moieties. Such labels are useful for the characterization and detection of amplification products using the methods and compositions of the present invention. The primer components may be present in the PCR reaction mixture at a concentration of, e.g., between 0.1 and 1.0 µM. The primer length can be between, e.g., 8-100 nucleotides in length. In order to aid in hybridization with the nucleic acid sequence, the primers in some embodiments have 50-60% G and C composition. In the choice of primer, it is preferable to have exactly matching bases at the 3' end of the primer but this requirement decreases to relative insignificance at the 5' end. In some embodiments, the primers of the invention all have approximately the same melting temperature. (2) Buffer. Exemplary buffers that may be employed, include, e.g., HEPES, borate, phosphate, carbonate, barbital, Tris, etc.-based buffers. See Rose et al., U.S. Pat. No. 5,508,178. The pH of the reaction should be maintained in the range of about 4.5 to about 9.5. See U.S. Pat. No. 5,508,178. The standard buffer used in amplification reactions is a Tris based buffer between 10 and 50 mM with a pH of around 8.3 to 8.8. One of skill in the art will recognize that buffer conditions should be designed to allow for the function of all reactions of interest. Thus, buffer conditions can be designed to support the amplification reaction as well as any enzymatic reactions associated with producing signals from probes. A particular reaction buffer can be tested for its ability to support various reactions by testing the reactions both individually and in combination. (3) Salt Concentration. The concentration of salt present in the reaction mixture can affect the ability of primers to anneal to the target nucleic acid. Potassium chloride is typically added up to a concentration of about 50 mM or more to the reaction mixture to promote primer annealing. Sodium chloride can also be added to promote primer annealing. (4) Magnesium Ion Concentration. The concentration of magnesium ion in the reaction can be critical to amplifying the desired sequence(s). Primer annealing, strand denaturation, amplification specificity, primer-dimer formation, and enzyme activity are all examples of parameters that are affected by magnesium concentration. Amplification reactions can contain, e.g., about a 0.5 to 2.5 mM magnesium concentration excess over the concentration of dNTPs. The presence of magnesium chelators in the reaction can affect the optimal magnesium concentration. A series of amplification reactions can be carried out over a range of magnesium concentrations to determine the optimal magnesium concentration. The optimal magnesium concentration can vary depending on the nature of the target nucleic acid(s) and the primers being used, among other parameters. A common source of magnesium ion is $MgCl_2$. (5) Carrier Proteins. Carrier proteins useful in the present invention include but are not limited to albumin (e.g., bovine serum albumin) and gelatin. (6) Deoxynucleoside Triphosphate Concentration. Deoxynucleoside triphosphates (dNTPs) are added to the reaction to a final concentration of about 20 µM to about 300 µM. Each of the four dNTPs (G, A, C, T) are generally present at equivalent concentrations. (7) Nucleic Acid Polymerase. A variety of DNA dependent polymerases are commercially available. For example, Taq DNA Polymerase may be used to amplify target DNA sequences. The PCR assay may be carried out using as an enzyme component a source of thermostable DNA polymerase suitably comprising Taq DNA polymerase which may be the native enzyme purified from *Thermus aquaticus* and/or a genetically engineered form of the enzyme. Other commercially available polymerase enzymes include, e.g., Taq polymerases marketed by Promega or Pharmacia. Other examples of thermostable DNA polymerases that could be used in the invention include DNA polymerases obtained from, e.g., *Thermus* and *Pyrococcus* species. Concentration ranges of the polymerase may range from 1-5 units per reaction mixture. The reaction mixture is typically between 20 and 100 µL. In some embodiments, a "hot start" methodology polymerase can be used to prevent extension of mis-priming events as the temperature of a reaction initially increases. Hot starts are particularly useful in the context of multiplex PCR. Examples of hot start methodologies include heat labile adducts attached to a polymerase or ligase requiring a heat activation step (typically 95° C. for approximately 10-15 minutes) or an antibody associated with the polymerase or ligase to prevent activation. Examples of different hot start methodologies are provided in the following articles (Chou, et al., *Nucleic Acids Research* 20: 1717-1723 (1992); Bassam, et al., *Bio Techniques* 14: 31-33 (1993); Horton, et al., *Bio Techniques* 16: 42-43 (1994); Kellogg, D. E., et al., *Bio techniques* 16: 1134-1137 (1994); Birch D. E., et al., *Nature* 381: 445-446 (1996); Bost, D. A., et al., *The FASEB Journal* 11: A1370 (1997)), which are incorporated herein by reference. (8) Other Agents. Assorted other agents are sometimes added to the reaction to achieve the desired results. For example, DMSO can be added to the reaction, though it is reported to inhibit the activity of Taq DNA Polymerase. Nevertheless, DMSO has been recommended for the amplification of multiple target sequences in the same reaction. Nonionic detergents (e.g. Tween-20) can also be added to amplification reactions. In addition, methylisothiazolinone (MIT) can be added to the reaction mixture.

Lyophilized particulates may also include one or more internal standards and/or one or more indicators, particularly fluorescent indicators, such as molecular beacons, scorpion primers, sunrise primers, and the like.

What is claimed is:

1. A reagent reservoir system for storing and activating a dried reagent, the system comprising:
    a) a chamber, which has a longitudinal axis, a fluid port, an exhaust port, and a retaining member; and
    b) the dried reagent, which is disposed in a reagent holding end of the chamber,
    wherein, the fluid port is disposed at the reagent holding end of the chamber, the retaining member is movably disposed in the chamber between the exhaust port and the dried reagent and is sized such that space between the interior of the chamber and the retaining member is smaller than the dried reagent, obstructing passage of the dried reagent from the reagent holding end toward the opposite end of the chamber.

2. The system of claim 1, wherein the retaining member has a density less than 1,000 $kg/m^3$.

3. The system of claim 2, the chamber further comprising a fixed member immobilized within the chamber between the exhaust port and the movably disposed retaining member, the fixed member obstructing passage of the movably disposed retaining member.

4. The system of claim 3, wherein the movably disposed retaining member is buoyant in liquid, and wherein the reagent chamber, the fixed member, and the buoyant retaining member are each composed of polymeric material.

5. The system of claim 1, wherein the dried reagent comprises an enzyme.

6. The system of claim 1, wherein the dried reagent comprises one or more lyophilized particulates.

7. The system of claim 1, wherein the dried reagent comprises nucleic acid amplification reagents.

8. The system of claim 7, wherein the dried reagent comprises one or more lyophilized particulates.

9. The system of claim 1, wherein the retaining member is buoyant in liquid.

10. A reaction cassette for conducting an assay on a sample, the reaction cassette comprising:
   a) a sample chamber having a sealable port at a first end and having a fluid port at a second end;
   b) a lysis chamber having a fluid port, the lysis chamber being capable of holding a lysis buffer; and the lysis chamber being selectably in fluid communication with the sample chamber;
   c) a reagent chamber having a first end and a second end, an exhaust port, a fluid port, and a retaining member, the reagent chamber being selectably in fluid communication with the lysis chamber;
   d) a dried reagent disposed at the second end of the chamber, wherein the exhaust port is at the first end of the chamber, the fluid port is at the second end, and the retaining member is movably disposed between the first and second ends of the reagent chamber and is sized such that space between the interior of the chamber and the retaining member is smaller than the dried reagent, obstructing to obstruct passage of the dried reagent through the reagent chamber; and
   e) a reaction chamber selectably in fluid communication with the reagent chamber.

11. The reaction cassette of claim 10, wherein the retaining member has a density less than 1,000 kg/m$^3$.

12. The reaction cassette of claim 10, wherein the dried reagent comprises one or more lyophilized particulates.

13. A reagent reservoir system for storing and activating a dried reagent, the system comprising:
   a) a chamber having first and second ends, an exhaust port, a fluid port, and a retaining member; and
   b) the dried reagent disposed in the second end of the chamber,
   wherein, the exhaust port is at the first end of the chamber, the fluid port is at the second end of the chamber, the retaining member is movably disposed in the chamber between the first and second ends and is sized such that space between the interior of the chamber and the retaining member is smaller than the dried reagent, obstructing passage of the dried reagent from the second end toward the first end.

14. The system of claim 13, wherein the retaining member has a density less than 1,000 kg/m$^3$.

15. The system of claim 14, the chamber further including a fixed member immobilized in the chamber between the exhaust port and the movably disposed retaining member through the chamber.

16. The system of claim 15, wherein the dried reagent comprises one or more lyophilized particulates.

* * * * *